United States Patent
Vilsmeier et al.

[11] Patent Number: 5,889,834
[45] Date of Patent: Mar. 30, 1999

[54] BLADE COLLIMATOR FOR RADIATION THERAPY

[75] Inventors: Stefan Vilsmeier, Poing; Michael Bertram, Heimstetten; Joseph Doyle, Munich, all of Germany; Ueli Graf, Mettmenstetten, Switzerland

[73] Assignee: Brainlab Med. Computersysteme GmbH, Heimstettn, Germany

[21] Appl. No.: 722,602

[22] Filed: Sep. 27, 1996

[30] Foreign Application Priority Data

Sep. 28, 1995 [DE] Germany ............ 195 36 188.1

[51] Int. Cl.⁶ .................................................. G21K 1/02
[52] U.S. Cl. ......................... 378/147; 378/150; 378/152
[58] Field of Search .................... 378/146, 147, 378/148, 151, 152, 160

[56] References Cited

U.S. PATENT DOCUMENTS

| | | | |
|---|---|---|---|
| 5,012,506 | 4/1991 | Span et al. ................................ | 378/152 |
| 5,166,531 | 11/1992 | Huntzinger .............................. | 378/152 |
| 5,297,037 | 3/1994 | Ifuku ...................................... | 378/152 |
| 5,433,048 | 7/1995 | Strasser ................................. | 52/288.1 |
| 5,591,983 | 1/1997 | Yoa ........................................ | 378/152 |

FOREIGN PATENT DOCUMENTS 0 245 768 B1  11/1987  European Pat. Off. .
42 03 610 C1   8/1994  Germany .

*Primary Examiner*—Don Wong
*Attorney, Agent, or Firm*—Armstrong, Westerman, Hattori, McLeland & Naughton

[57] ABSTRACT

The accuracy of radiation therapy is enhanced with the blade collimator of the claimed invention. Particularly, this collimator includes a support device for supporting at least two sets of radiation attenuating blades in a single plane or layer. The blades are reciprocally movable within this support. Shaping of the therapy may be increased by constructing the blades to include a varying width increasing from the central blade toward the exterior blades.

24 Claims, 3 Drawing Sheets

BLADE COLLIMATOR FOR RADIATION THERAPY

The invention relates to a blade collimator for radiation therapy of the class described in the introductory clause of claim 1.

Blade collimators are accessories of linear accelerators that are used especially to irradiate tumors. They were developed to limit the area of radiation, to protect vital tissues from radiation, and thus to replace the traditional shielding blocks, which must be made to order for each tumor and are expensive to manufacture. Although these shielding blocks, because they are cast separately for each tumor, naturally permit very good adjustment to the shapes of tumors, it was desirable to create and employ relatively adjustable, reusable devices for limiting the area of radiation, using blade collimator technology, suitable for a range of tumor shapes.

Basically, blade collimators have two sets of separately movable blades facing each other; their front faces are pushed together in such a way that the blades circumscribe an open area between the front faces that coincides fairly well with the contour of the tumor to be treated. The blades can be moved manually, electrically, or mechanically by means of spring mechanisms.

Two basic classes of blade collimators are known to prior art. In the first class, relatively wide blades, often made of tungsten, are used to treat larger tumors. The width of blades for such collimators ranges from 6 mm to 1 cm, which permits irradiation of large areas of great width up to 60 cm.

The front faces of the blades have a rectangular shape. This causes a problem in the use of collimators with wide blades: when the front faces are moved toward the contour of the tumor, it proves impossible to achieve a satisfactory match with the shape of the tumor. If the front faces of the blades are moved up to their first point of contact with the contour of the tumor, then the staircase pattern thus formed leaves open relatively large areas through which radiation can strike and damage vital tissue. This becomes an especially serious problem when treating the brain. If the blades are moved up in such a way that no vital tissue is left exposed to the radiation, this causes the opposite problem: the "stair landings" that are formed by the front faces of the blades cover parts of the tumor, which then cannot be treated. Moreover, the scattering of radiation reaches a high level with such collimators; the dose gradient becomes small. Overall, it may be concluded that the collimators with wide blades described above can indeed be used to irradiate large areas, but cannot be adequately adjusted to match the shape of the object to be irradiated.

In order to solve this problem, a second class of blade collimators that employ very narrow blades was developed. Such blades, which are as narrow as 1 mm, in principle permit good adjustment of the localized radiation area to the shape of the tumor. Yet there are substantial disadvantages associated with devices of this type, particularly as regards the size of the area that can be irradiated.

The number of blades that can be used is limited. This is because each blade must be able to be independently shifted by mechanical means, for which purpose each blade is generally equipped with an activating and shifting mechanism. These shifting mechanisms—which can be electric motors, for example—must all be mounted on the collimator or its support. This necessarily places an upper limit on the number of blades because too many of them would make the collimator, together with its support and activating mechanisms, too large and too heavy.

A limited number of blades of lesser width restrict such a collimator to the irradiation of very small areas. Therefore, despite the relatively good adjustment, such a collimator is limited to a rather small area of application (e.g. the irradiation of small tumors).

A contour collimator for radiation therapy is known from European patent number specification 0 245 768, which describes an effective adjustment device for the blades. Another contour collimator is known from German patent specification number 42 03 610; it employs a spring mechanism and a readjustment device for the blades. These two collimators of prior art also operate with blades of uniform width; that is, they are also beset by the problems associated with narrow or wide blades that are described above.

The goal of the present invention is to provide a blade collimator for radiation therapy that solves the aforementioned problems. In particular, a blade collimator will be suggested that makes possible both good adjustment to the contour of the object to be irradiated and irradiation of relatively large areas.

This goal is attained with a blade collimator designed according to the characterization part of claim 1.

The subsidiary claims describe preferred embodiments of the blade collimator according to the invention.

The main advantage of using blades of various widths within a blade field of the collimator is that it becomes possible to use narrow blades at those places where a precise adjustment to the contour to be irradiated is necessary, while wider blades can be employed at those places where they provide adequate adjustment—for example, those tumor contours that are relatively straight, against which the wide blades can be laid lengthwise with a good fit. By using both narrow and wide blades, it becomes possible to irradiate relatively large areas, while precise adjustment can be made to the difficult sites with the narrow blades, all while using the usual number of blades. This ensures that the diseased tissue is completely irradiated, while vital tissue is shielded from radiation and so remains undamaged. Thus the invention incorporates the advantages of the blade collimators known to prior art; it has the good adjustability of the narrow blades and the adequate irradiation field size of the wide blades, while compensating for the disadvantages described above.

A blade collimator according to the invention can be designed in several advantageous ways.

In one embodiment, several adjacent blades are grouped in sets of uniform width. This configuration is especially well suited to objects requiring irradiation having a contour that is highly irregular in at least one area, but that is regular in other places, so that sets of the narrower blades can cover the irregular site, while sets of the larger blades cover the regularly shaped contours.

In another advantageous embodiment, the width of the blades in the collimator increases from inside to outside. The shape of many tumors is characterized by irregular contours near the center. A collimator whose blade width increases from inside to outside can be especially well adjusted to such tumors, while the tumors may occupy larger areas. With this design in particular, the width arrangement of the blades can be symmetrical to an axis of symmetry lying in the direction of travel. In this way, the drive with its activating elements can be executed regularly and therefore inexpensively in terms of design, while a wide range of application is maintained for using the collimator.

The possible means for adjusting the blade positions for the collimator according to the invention range from shifting by hand, through adjustment to a preformed contour model, to very expensively operated adjustment and activating mechanisms. In one embodiment of the invention, devices are mounted on the blade support for moving the blades separately or in sets; these devices are driven by electrical and/or mechanical devices, especially by springs, connecting rods or electric motors. This makes it possible to couple the shifting devices and their activating mechanisms to a control unit, which controls the activation and path adjustment of the blades by means of stored patient data, especially data consisting of x-rays, computer tomograms or nuclear spin resonance tomograms. Such a control unit, which might operate by means of a computer, works together with the blade collimator according to the invention to facilitate precise adjustment to the irradiation contour, especially when radiation comes from various directions. Patient data or contours of the type described above are three-dimensional, so that the computer can adjust the blade collimator to the calculated contour with a good fit from any direction of exposure.

In another embodiment of the invention, the sets of blades are arranged with their support or such that they rotate relative to the support. The rotation of the entire array (i.e. the sets of blades with the support or the sets of blades on the support) makes possible a further improvement in the adjustability of the exposure boundary to the contour to be irradiated. Through such rotation, one can ensure that the narrower blades come to rest on irregular points of the contour, while regular sites are covered by wide blades. Connected with a sensor, which via the control unit monitors both the contour of the object to be irradiated and the rotational angle of the blade arrangement, such adjustments can be carried out under computer control.

While the preceding discussion has assumed that the blades are permanently mounted on their support, another design according to the invention is conceivable in which the blades come as modules so that sets of them are interchangeable. With the use of an activating and shifting mechanism suited to all blade modules, a still wider range of adjustment to the size and/or contour of the object to be irradiated can be ensured through the selection of sets of blades of appropriate width.

Possible end-on radiation through the sets of blades can be prevented by giving them a special shape. In particular, blades designed according to the invention can be equipped with interlocking teeth on their side faces. Another possibility is to make use of overfocusing; in other words, to design the blades such that they are leak-proof and have a prismatic shape relative to an imaginary radiation source, whereby the imaginary radiation source lies higher than the actual radiation source used in the treatment. This yields better radiation absorption in the actual irradiation process.

In another preferred embodiment of the blade collimator according to the invention, an additional blade is inserted between two blades; the former is positioned by means of mechanical devices such that its front face according to the direction of travel of the blades always occupies an essentially intermediate position between the front faces of the two adjacent blades. In this configuration, the number of activating and control mechanisms, as well as the weight, can be reduced, because only every other blade requires a drive. Yet this arrangement retains the good adjustment to the contours without the otherwise usual formation of steps.

Preferably, the sets of blades of a blade collimator according to the invention consist of 20 to 32 blades, with a preferred embodiment equipped with 26 blades. One advantageous configuration for 26 blades would be to arrange the blades symmetrically from the outside to the inside so that three blades 4 mm in width, three blades 3 mm in width and seven 2 mm in width are provided for each side. A configuration such as this is low in overall weight, easily controllable, and can block out relatively large irradiation contours with a very good fit.

Very narrow sets of blades, which in the case of the configuration according to the invention come into play when very narrow blades of uniform width are used, can entail a problem with secondary position measurement. Such secondary position measurements are especially needed when motor-driven sets of blades are used.

The drive motors have an encoder which can report back the primary blade position; in troublesome cases, the motors can execute turns, even when the corresponding blade stops for any reason, as when it locks up. After such "no-load racing," the encoder reports a position that does not match the real position of the blade. In order to adjust for this mistake, blade collimators have a secondary position measurement device that ascertains the real position of the blade via rods connected to the blades; the ends of these rods communicate with individual movable contacts. These rods, as well as the movable contacts, occupy adjacent positions in a relatively wide layout that is necessitated by design considerations.

Normally, in collimators with wide blades, the latter could be connected in a simple manner (e.g. directly) to the straight rods of the position measurement device. With narrow blades, which entail blade areas that are much narrower than the overall array of rods belonging to the secondary position measurement device, this is not possible.

In terms of the invention, this problem is solved by a blade collimator characterized by individual blades whose upper edges, towards the back, are equipped with oblong connecting cords whose other ends engage the rods of a secondary position measurement device; seen from the direction of travel of the blades, the connecting cords spread out upwards in roughly a fan shape up to the rods' contact points, which are more widely separated than the blades.

In this design, the connecting cords are made of flat strips, especially metal strips, which bend in their course from the edges of the blades to the contact points on the rods of the position measurement device and whose end segments are preferably straight.

Secondary position measurement can be carried out at any time with the solutions described above, even with very narrow blade fields.

Another problem with narrow blade collimators of this type, in which the blades have tapped holes in the direction of travel where threaded rods turn during the adjustment operation, is that narrow blades can accommodate only small tapped holes. However, the small-diameter threaded rods that are inserted into these holes are unstable, especially if one recalls that in the vertical position, the weight of a blade made of tungsten rests on the threaded rod and that frictional forces also come to bear during movement.

Although the usual blades are offset for radiation shielding and conveyance by each other, this does not permit the tapping of larger-diameter holes because the individual sections of the blades all have the same limited thickness.

The blade collimator according to the invention is designed to solve this problem, and for this purpose is characterized by blades which, seen from the direction of travel, exhibit from top to bottom a cross-sectional shape with widened sections on both sides of the bisecting line of the individual blades, and matching narrowed sections. In each case, the adjacent, identically shaped blades exhibit their widened sections and narrowed sections at corresponding longitudinally displaced sites, so that the side faces of the blades nestle against each other in essentially flat contact. Preferably, holes are tapped as counterparts to a drive-threaded rod in each of the widened cross-sectional areas of the blades.

This offset configuration of the blades makes it possible to bring the individual blades into proper position relative to one another, to provide radiation shielding perpendicular to the direction of travel, as well as the tapping of larger-diameter holes and thus an increase in stability. Furthermore, with this symmetric design, sets of blades can be deployed on both sides of the collimator; the blades of opposing, identically shaped sets can slide by each another with ease as needed.

The arrangement and housing of the separate drive motors presents another problem in the blade collimators described above, with their narrow blade configuration. Electric motors with diameters of less than approximately 16 mm are not commercially available. Although the motors are arranged in a height-staggered configuration, it is not possible to reach each blade in a small blade area in a straight line via drive shafts and drive threaded rods that are attached to the motors. The only traditional solution is to utilize flexible threaded rods, which must be made of plastic. Unfortunately, they are unstable, and generate abrasion that can impair or stop the movement of the blades. Use of grease can clog up the entire apparatus with prolonged use.

This problem too can be solved by a blade collimator according to the invention in which the blades are moved by electric motors and each electric motor has a drive shaft and a drive threaded rod; the problem is solved by staggering the motors one behind the other in the direction of travel of the blades.

Such a longitudinally staggered configuration of motors permits every blade to be driven with a threaded rod running in a straight line. More than sufficient room remains between motors arranged in the same longitudinal position to permit the drive shaft or the threaded rod of a motor situated behind it to pass through.

Embodiments of the blade collimator according to the invention are described more fully below with reference to the attached figures.

Figure 1:
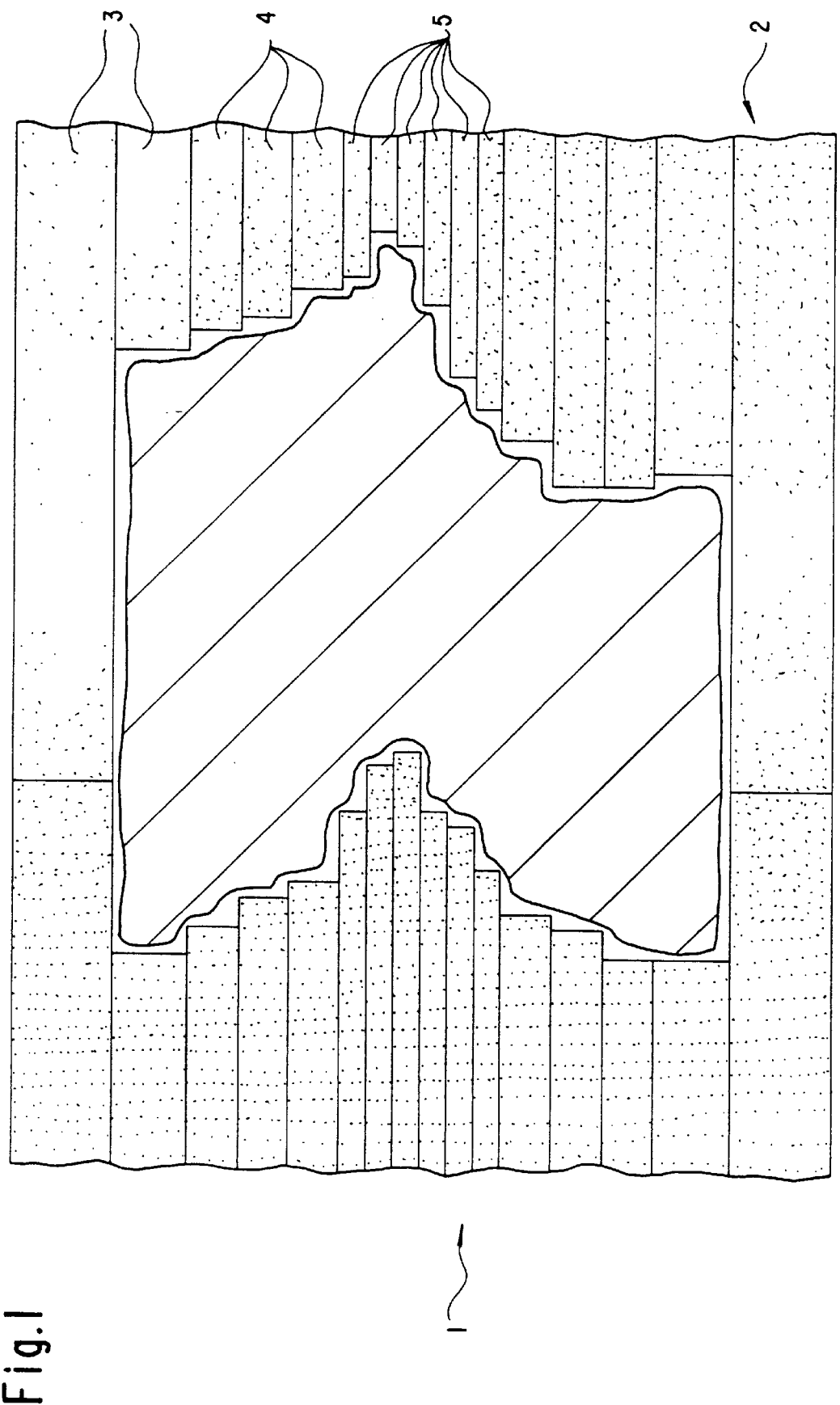
FIG. 1 is a major cross-section of a blade configuration belonging to a blade collimator depicted as an embodiment of the invention.

FIG. 1 shows a left set of blades 1 and a right set of blades 2. To simplify the illustration, each set of blades is shown with only 16 blades, whereas the collimators according to the invention that are normally produced can have very many more blades. The configuration of blades depicted in the drawing is variable as regards their displacement. However, there is a symmetrical number of blades relative to two perpendicular axes. The blades in each set can be grouped in sets 3, 4 and 5 of uniform width; due to their symmetrical arrangement, they are labelled with references only in one corner of the drawing.

Each set of blades 1, 2 consists of four outer wide blades, six medium-width blades adjoining them, and six inner narrow blades, which in this manner comprise the outer blade sets, the middle blade sets 4 and the inner blade sets 5.

The blades are depicted in section on the right and left sides of the drawing. Adjustment devices (not shown), which engage the left and right terminal faces of the individual blades (also not shown), are driven by activating mechanisms such as electric motors.

In this drawing, the blades are shifted toward the middle of the collimator from left and right for irradiation of tumor contour K. Contour K is drawn in and hatched for purposes of illustration.

The blades are shifted for radiation shielding to match the contour of the tumor, so that the inner open area is irradiated, while the region shielded by the blades remains unexposed. Although the blades are moved separately, they can be grouped in blade sets 3, 4 and 5 as described above. It is evident that the narrow blades contained in set 5 run up against the central part of the tumor, which has a very irregular contour. This permits a very good match of the radiation shielding to this irregular contour; only very small "stair-shaped" radiation steps remain, which means the vital tissue can be protected very well. For the somewhat less irregular contour in the outer middle range, the medium-width blades of set 4 provide an adequate fit, while the wider blades of blade set 3 provide a very good match to the regular contours of the outer part of the tumor.

Rotation of the blade field brings it into the best possible position for the tumor to be treated. It is clear that a variation in the width of the blades facilitates excellent adjustment to a contour with the narrow blades, whereas the deployment of medium-width and wide blades permit shielding of contours of relatively large dimensions.

The use of traditional blade collimators with blades of uniform width would present great difficulties in the case presented here, because if these blades were very narrow, the collimator would have to be kept small due to the limited selection of blades, meaning that the entire area could not be irradiated. Although in this case the use of traditional wide blades of uniform width could cover the entire area of exposure, large radiation leaks would occur in areas with irregular contours, thus exposing vital tissue to damaging radiation.

The collimator according to the invention solves these problems with its blades of varying width, and combines the advantages of both classes mentioned above, as becomes clear in the illustrated embodiment.

Figure 2:
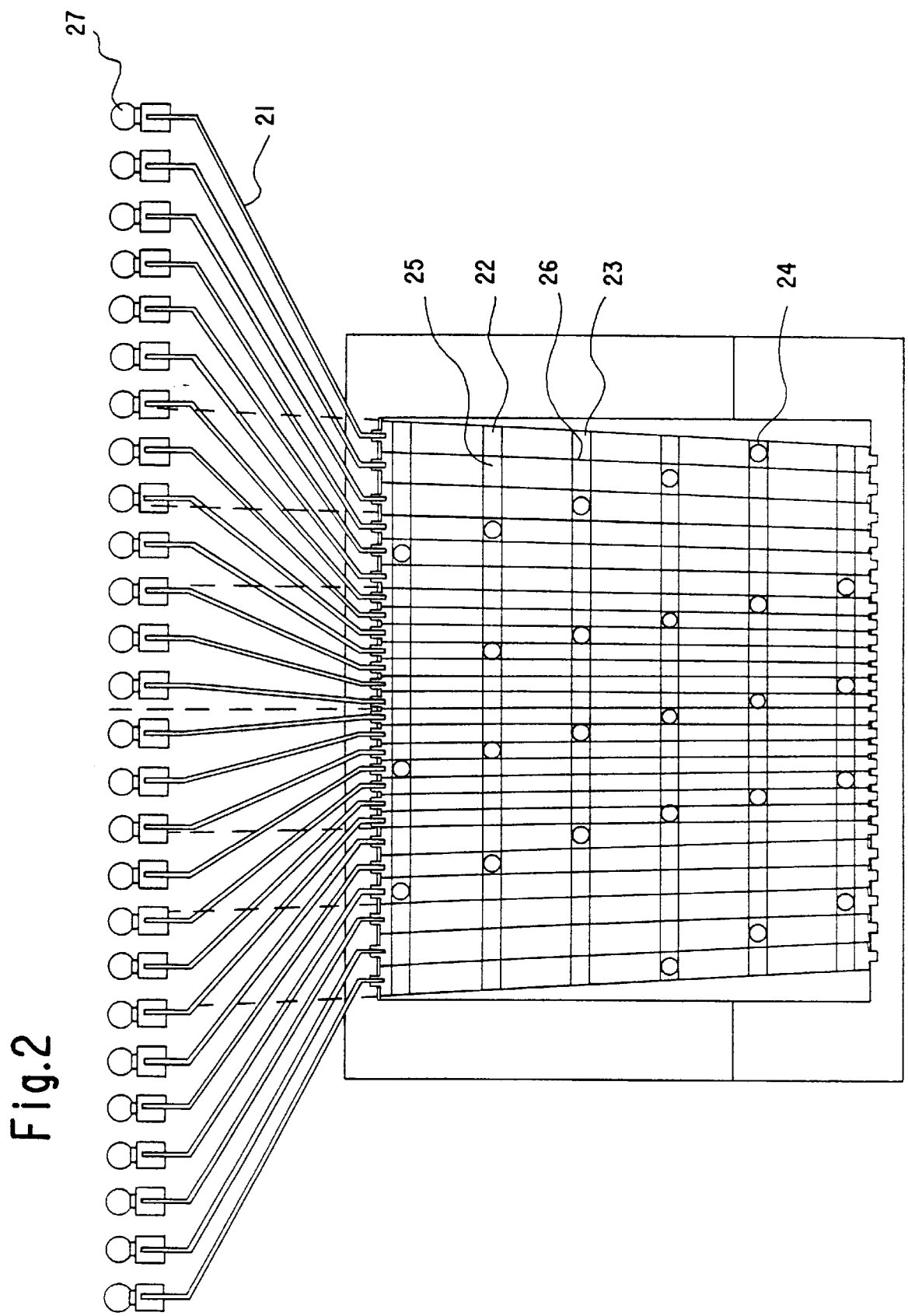
FIG. 2 shows a view of a set of blades of a collimator according to the invention in the direction of travel of the blades with connecting strips mounted on the upper side of the blades, and these connecting strips engage a position measurement device.

FIG. 2 shows a view of a set of blades belonging to a collimator according to the invention in the direction of travel of the blades with connecting strips that engage a position measurement device and are mounted on the upper side of the blades.

In the blade collimator depicted here, oblong connecting cords (21) are mounted on the upper edges, toward the rear, of the individual blades; the other ends of these connecting cords engage the rods of a secondary position measurement device, which is not shown, via a mechanism such as a ball connector (27). Seen from the direction of travel of the blades, the connecting cords (21) spread out upwards in roughly a fan shape to meet contact points on the rods, which are more widely separated than the blades. The connecting cords (21) consist of flat metal strips that bend in their course from the edges of the blades to the contact points on the rods of the position measurement device (the bend runs perpendicular to the plane of the drawing and is therefore not visible); the end segments of these strips are straight.

One method of connecting the lower ends of the metal strips to the blades is by soldering.

FIG. 2 also shows that the blades, as seen from the direction of travel, exhibit from top to bottom a cross-sectional shape with widened sections (23) on both sides of the bisecting line of the individual blades, as well as matching narrowed sections (22). In each case, the adjacent, identically shaped blades have their widened sections (25) and narrowed sections (26) at corresponding, longitudinally displaced sites such that the side faces of the blades nestle against each other in essentially flat contact. Tapped holes (24) as counterparts to a drive-threaded rod are found in the widened cross-sectional areas of each blade. They can be relatively wide in diameter and therefore accommodate stable threaded rods.

Figure 3:
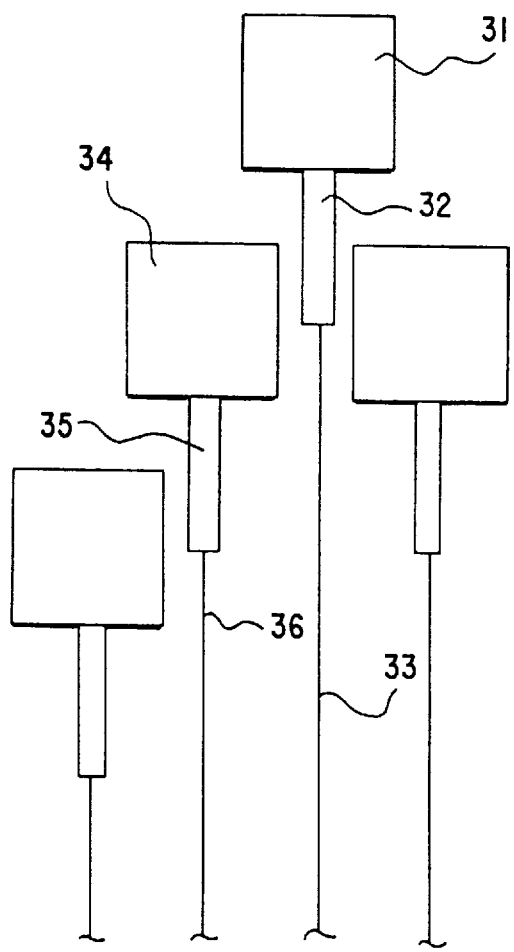
FIG. 3 is a schematic diagram of a staggered configuration of motors according to the invention.

FIG. 3 is a schematic diagram of a staggered motor configuration of the invention. In a blade collimator in which the blades are driven by electric motors (31, 34) and the electric motors each have a drive-shaft (32, 35) and a drive-connecting rod (33, 36), the motors (31, 34) are arranged in a staggered pattern one behind the other in the direction of travel of the blades. Depending on the number of motors, the stagger can be two-step or, as illustrated here, three-step. The stagger can of course have still more steps in the longitudinal direction. The motors are also usually height-staggered—that is, staggered in the direction perpendicular to the plane of the drawing.

It is clear from the schematic diagram of FIG. 3 that with a configuration such as this, the shaft (32) or the threaded rod (33) can pass between the two motors lying in front of it with ease, thus permitting a linear drive for the blades.

We claim:

1. Blade collimator for radiation therapy, comprising a support device,
    two opposing sets of blades mounted in one layer in said support device, each blade capable of reciprocable movement in said support device and having a dimension perpendicular to the movement,
    each set of blades comprising a central blade adjacent to the blades of the other set, an exterior blade, and a blade interposed between the central blade and the exterior blade, the dimension of the exterior blade being greater than the dimension of the interposed blade and the dimension of the interposed blade being greater than the dimension of the central blade.

2. Blade collimator according to claim 1 in which the dimensions of several adjacent blades of each set are equal.

3. Blade collimator according to claim 1 in which the blades are leak-proof against radiation by means of reciprocal interlocking of teeth.

4. Blade collimator according to claim 1 in which the dimensions of the respective blades are symmetrical to an axis of symmetry in a direction of the movement.

5. Blade collimator according to claim 1 in which mechanisms for moving the blades separately or in sets are mounted on the blade support, and the mechanisms are activated by at least one of electrical and mechanical devices.

6. Blade collimator according to claim 5 in which the devices are coupled to a control unit that controls the activation and path adjustment of the blades by means of stored patient data.

7. Blade collimator according to claim 6 in which the sets of blades are arrayed with their support or such that they rotate relative to it.

8. Blade collimator according to claim 1 in which sets of blades in modular form are interchangeable.

9. Blade collimator according to claim 1 in which the blades are leak-proof against radiation by means of overfocusing.

10. Blade collimator according to claim 1 in which an additional blade is inserted between two blades and the additional blade is positioned by mechanical devices such that its front face in the direction of movement of the blades always occupies an essentially intermediate position between the front faces of the two blades adjacent to it.

11. Blade collimator according to claim 1 in which the sets of blades consist of from 20 to 32 blades.

12. Blade collimator according to claim 11 with 26 blades in which each set has:
    3 blades 4 mm in width,
    3 blades 3 mm in width and
    7 blades 2 mm in width.

13. Blade collimator according to claim 1, in which an end of oblong connecting cords are mounted on upper edges, toward the rear, of the individual blades, whereby other ends of the connecting cords engage rods of a secondary position measurement device and the connecting cords, seen from the direction of movement of the blades, spread out upwards in roughly a fan shape to meet contact points on the rods, which are more widely separated than the blades.

14. Blade collimator according to claim 13 in which the connecting cords consist of flat strips that bend in their course from the blades to the contact points on the rods of the position measurement device.

15. Blade collimator according to claim 1, in which the blades, as seen from the direction of movement, exhibit from top to bottom a cross-sectional shape with widened sections on both sides of a bisecting line of the individual blades, as well as matching narrowed sections, whereby the adjacent, identically shaped blades exhibit their widened sections and narrowed sections at corresponding longitudinally displaced positions, so that the side faces of the blades nestle against each adjacent blade in essentially flat contact.

16. Blade collimator according to claim 15 in which tapped holes as counterparts to drive threaded rods are created in the widened cross-sectional areas of each blade.

17. Blade collimator according to claim 5, in which
    the blades are moved by electric motors, and
    the electric motors each have a drive shaft and a drive threaded rod, whereby
        the motors are arranged one behind the other in a staggered configuration in the direction of movement of the blades.

18. Blade collimator according to claim 13, in which
    the blades are moved by electric motors, and
    the electric motors each have a drive shaft and a drive threaded rod, whereby
        the motors are arranged one behind the other in a staggered configuration in the direction of movement of the blades.

19. Blade collimator according to claim 15, in which
    the blades are moved by electric motors, and
    the electric motors each have a drive shaft and a drive threaded rod, whereby
        the motors are arranged one behind the other in a staggered configuration in the direction of movement of the blades.

20. Blade collimator according to claim 5 in which the mechanisms are activated by springs.

21. Blade collimator according to claim 5 in which the mechanisms are activated by connecting rods.

22. Blade collimator according to claim 5 in which the mechanisms are activated by electric motors.

23. Blade collimator according to claim 5 in which the stored patient data includes at least one of x-rays, computer tomograms or nuclear spin resonance tomograms.

24. Blade collimator according to claim 14 in which the connecting cords consist of flat metal strips, and whose end segments are straight.

* * * * *